United States Patent
Fiala et al.

(10) Patent No.: US 8,066,767 B2
(45) Date of Patent: Nov. 29, 2011

(54) INTRAOCULAR LENS

(75) Inventors: Werner Fiala, Vienna (AT); Christine Kreiner, Munich (DE)

(73) Assignee: Acri.Tec GmbH, Hennigsdorf (DE)

(*) Notice: Subject to any disclaimer, the term of this patent is extended or adjusted under 35 U.S.C. 154(b) by 0 days.

(21) Appl. No.: 12/484,282

(22) Filed: Jun. 15, 2009

(65) Prior Publication Data

US 2009/0270983 A1      Oct. 29, 2009

Related U.S. Application Data (63) Continuation of application No. 10/559,376, filed as application No. PCT/EP2004/006074 on Jun. 4, 2004, now abandoned.

(30) Foreign Application Priority Data

Jun. 6, 2003 (DE) .................. 103 25 841

(51) Int. Cl.
*A61F 2/16* (2006.01)
(52) U.S. Cl. ........................ 623/6.23
(58) Field of Classification Search ............ 623/4.1, 623/6.23, 6.24
See application file for complete search history.

(56) References Cited

U.S. PATENT DOCUMENTS

| | | |
|---|---|---|
| 4,504,982 A | 3/1985 | Burk |
| 5,796,462 A | 8/1998 | Roffman et al. |
| 6,533,416 B1 | 3/2003 | Fermigier et al. |
| 2001/0051826 A1 | 12/2001 | Bogaert et al. |
| 2002/0154271 A1 | 10/2002 | Donitzky et al. |

FOREIGN PATENT DOCUMENTS

| | | |
|---|---|---|
| EP | 0765468 B1 | 10/2002 |
| EP | 1248093 A1 | 10/2002 |
| JP | 05-019215 | 1/1993 |
| WO | 0189424 A1 | 11/2001 |

OTHER PUBLICATIONS

K. Suzuki, I Ogura, T. Ose: "Measurement of spherical aberrations using a solid-sate image sensor", Applied Optics, Bd. 18, Nr. 22, Nov. 15, 1979 pp. 3866-3871 (XP002297938).

Datenbankauszug (Medline): Klinische Monatsblaetter fuer Augenheilkunde, vol. 214, Apr. 1999, pp. 246-250. (One Page).

*Primary Examiner* — William H. Matthews
(74) *Attorney, Agent, or Firm* — Crowell & Moring LLP (57) ABSTRACT

The invention concerns an intraocular lens with negative spherical aberration and a method of determining the refractive power of intraocular lenses. In the environment of immersion medium the intraocular lens refracts an incoming wave with an elliptically oblongly curved wave front into an outgoing wave with a substantially spherical wave front.

2 Claims, 9 Drawing Sheets

INTRAOCULAR LENS

The invention refers to an intraocular lens (IOL) and a method of determining the imaging properties of intraocular lenses.

Lenses of that kind are known. The topography of conventional intraocular lenses generally involves spherical curved surfaces whose imaging properties however are not ideally suited to producing an image on the retina of the human eye. Known methods of determining the imaging properties of intraocular lenses generally presuppose basically spherically curved surfaces.

The object of the invention is to provide an intraocular lens whose imaging properties produce an image of improved quality on the retina. A further object of the invention is to provide a method of determining the imaging properties of the intraocular lens, which method provides reliable results independently of the topographical nature of the lens.

According to the invention that object is attained by an intraocular lens with negative spherical aberration. Conventional, spherically curved intraocular lenses of positive refractive power have a positive spherical aberration, that is to say they refract an incoming wave with a plane wave front into an outgoing wave with an oblate elliptically curved wave front. The focus of such a lens is accordingly not punctiform. In comparison the intraocular lens according to the invention is preferably of such a configuration that, in the environment of immersion medium, in particular the in vivo environment (refractive index 1.336) in the eye it refracts an incoming wave with an oblate elliptically curved wave front into an outgoing wave with a wave front which is substantially spherical. In that way the imaging properties of the cornea of the eye, which is in front of the IOL, are better taken into consideration and the effect is that more accurate focusing on the retina is possible.

Such imaging properties are preferably achieved by the refractive index and the curvature of the lens surfaces being so selected that the lens at the centre has a refractive power D of greater than or equal to +3 dioptres (dpt) in the immersion medium and that in the environment of air an incoming wave with a substantially plane wave front is refracted into an outgoing wave with a hyperbolic wave front.

Figure 1:
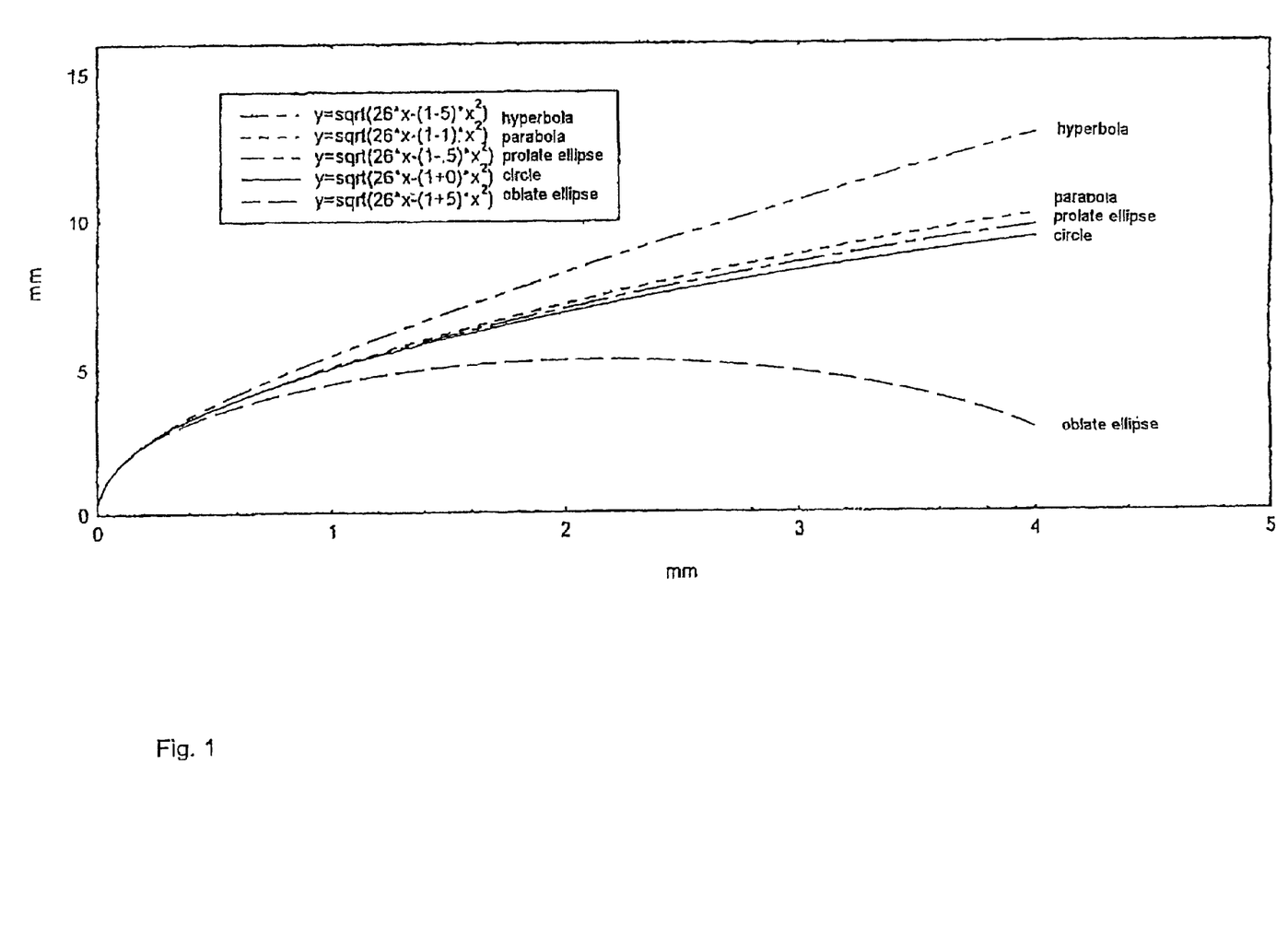
FIG. 1 shows a view of the curvature of a curve described by equation (1) for various asphericity values, and for p=13.

The shape of the curvature of the wave fronts and also the curvature of the lens surfaces can be described by the following function:

$$y^2 = 2px - (1+asph)x^2 \quad (1)$$

wherein x coincides with the direction of light propagation or the lens thickness, y specifies the direction perpendicular thereto, radially outwardly with respect to the lens centre, p is a parameter and asph is so-called asphericity, that is to say a measure for the deviation of the curvature of the lens surface from a spherical shape. The shape of the lens surface or wave front is shown in section for different asphericities in FIG. 1. With an asphericity of greater than 0 the equation accordingly describes an ellipse whose minor axis in the x-direction (illustrated on an extended scale) is less than that in the y-direction (oblate). If the asphericity is equal to 0, a circle is described. If it is between 0 and −1 (in each case excluding the limit values), an ellipse is described, whose major axis in the x-direction is greater than that in the y-direction (prolate). If the asphericity is −1 then equation (1) describes a parabola and if its value is less than −1 it then describes a hyperbola.

Preferably the hyperbolic wave front of a wave produced from an incoming plane wave by the lens according to the invention has an asphericity ($asph_{OUT}$) of less than or equal to −1. Also the intraocular lens preferably has at least one convexly curved surface whose curvature is of an asphericity ($asph_L$) of less than or equal to −1.

The invention is described in greater detail hereinafter by means of embodiments by way of example with reference to the Figures in which.

The imaging conditions of the human eye are now investigated taking into account the IOL according to this invention. As is known the cornea has a refractive index of about 1.37, topographically it essentially represents an asperoidal shell. It has a negligibly slight influence on refraction of an incoming wave. Refraction of the incident light depends rather on the one hand on the curvature which is predetermined by the topography of the cornea and on the other hand on the refractive index of the immersion medium behind the cornea (aqueous humour). As is known, that has a refractive index of 1.336. The topography of the cornea is characterised by the asphericity ($asph_c$), for which the literature specifies values of $asph_c=-0.26+0.18$ (Kiely et al, in G Smith et al, Vision Research 41, 2001, 235-43) and $asph_c=-0.18+0.15$ (Guillon et al, loc. cit.). In accordance with those literature values it can be assumed that the cornea of the human eye is generally elliptically curved. For the following considerations, a value range of $asph_c=-0.56$ to 0 is therefore assumed for the asphericity of the cornea, in order to ensure that practically all human cornea asphericities occurring in nature are embraced. In that respect it is to be observed that the upper limit value ($asph_c=0$) corresponds to a cornea with spherical curvature.

In addition the topography of the cornea is characterised by its surface refractive power at the centre point, that is to say on the optical axis. A range of 40 to 50 dioptres (dpt) is assumed for that purpose, whereby the range of the surface refractive power of the cornea, which actually occurs in nature and which in accordance with knowledge at the present time is at 43 dpt as an average value, is covered both towards higher and also lower values.

Figure 2:
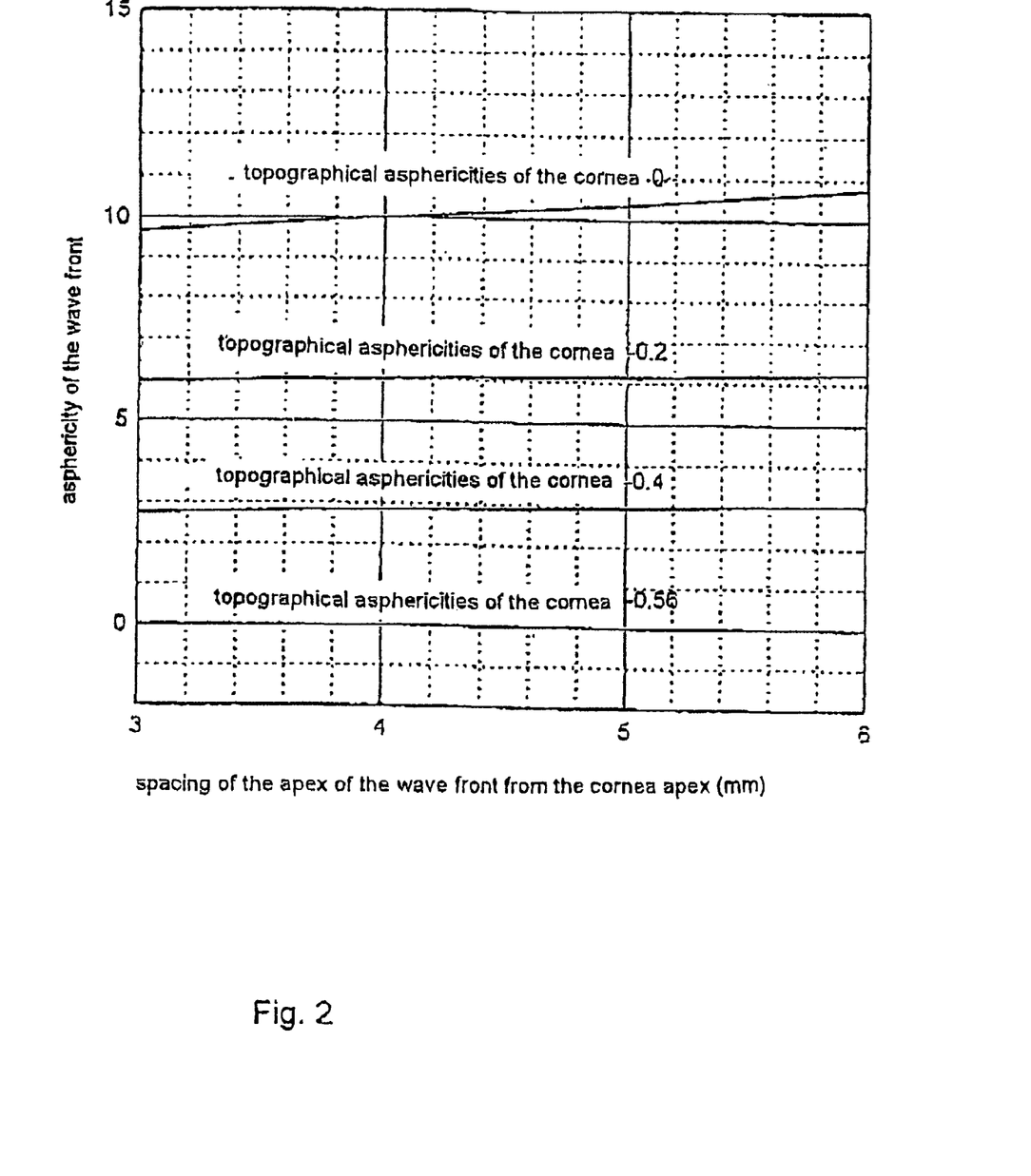
FIG. 2 shows a diagram of the asphericity of an outgoing wave for various topographical asphericities of the cornea with a corneal refractive power at the centre of 40 dioptres.
Figure 3:
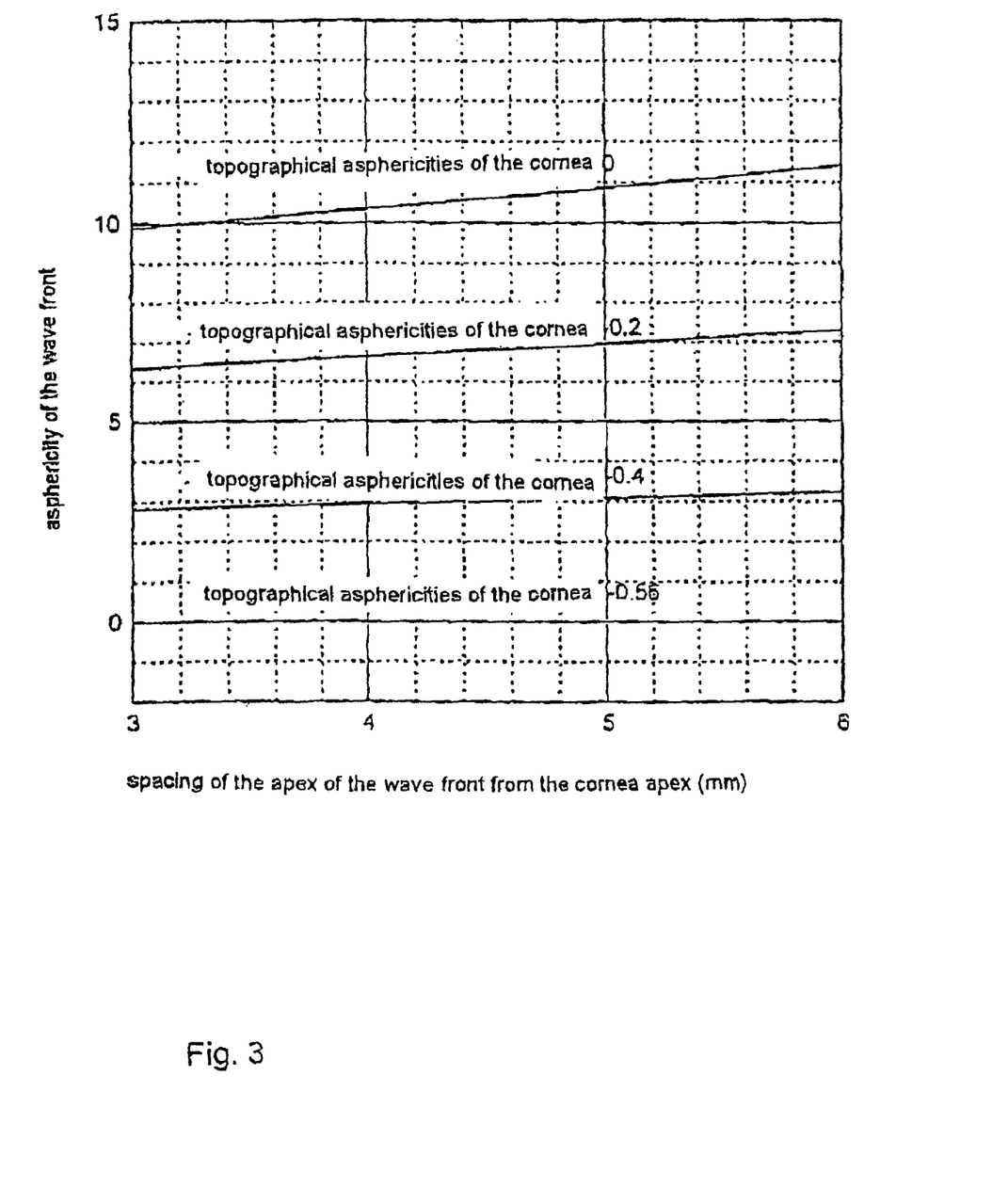
FIG. 3 shows a diagram of the asphericity of an outgoing wave for various topographical asphericities of the cornea with a corneal refractive power at the centre of 50 dioptres.

FIGS. 2 and 3 show the asphericity ($asph_{IN}$) of a wave refracted by the cornea upon incidence of a plane wave, that is to say a wave with a plane wave front, like for example light which is emitted by a point at an infinitely far distance. That depends on the topographical asphericity of the cornea and the spacing of the apex of the wave front from the apex of the cornea (abscissa value). The spacing between the centre of the intraocular lens and the front apex point of the cornea in the human eye, which is between a minimum of 3 mm and a maximum of 6 mm, is taken as the basis for the range of that value. FIG. 2 specifies the conditions in the case of a cornea with a central surface refractive power of 40 dpt. It can be seen therefrom that the asphericity of the refracted wave front which impinges on the intraocular lens ranges between the limit value $asph_{IN}=0$ with a topographical asphericity of the cornea $asph_C=-0.56$ and the limit value $asph_{IN}=10.8$ with a topographical asphericity $asph_C=0$. On the basis of a central surface refractive power of the cornea of 50 dpt, see FIG. 3, the asphericity of the refracted wave front $asph_{IN}$ impinging on the intraocular lens is between 0 and +11.4. Overall therefore it can be established that the asphericity of that wave front is always in the last-mentioned range, and the wave front is therefore either spherical ($asph_{IN}=0$) or otherwise always oblate elliptically curved ($asph_{IN}>0$). In other words the cornea has a positive spherical aberration as it refracts the rays at the edge more greatly than those at the centre. With this in mind, an IOL with negative spherical aberration is required in order to refract the aspherical wave coming from the cornea so as to achieve improved image formation on the retina of the eye.

Preferably the IOL according to the invention is so designed that, in the environment of immersion medium, an incoming wave with an oblate elliptically curved wave front is refracted into an outgoing wave with a substantially spherical wave front, wherein the refractive power of the IOL is to be so selected in dependence on the eye of the patient that the centre of the outgoing waves is on the retina of the eye.

The IOL according to the invention can assume various configurations: in accordance with a first embodiment, at its centre, in the environment of the immersion medium, it has a refractive power $D_I$ of at least +3 dpt and the refractive power decreases towards the edge of the lens. In addition, by way of example, a refractive index of 1.46, a lens diameter of 6 mm and an axis-parallel edge thickness of 0.25 mm is assumed to apply.

Figure 4:
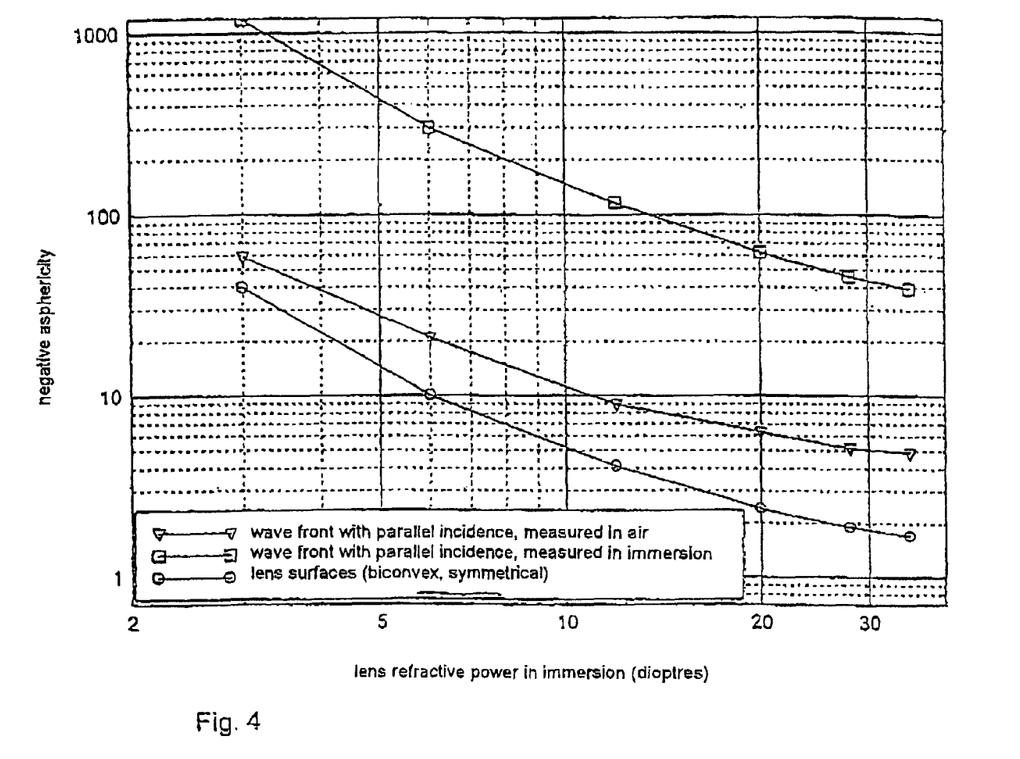
FIG. 4 shows a diagram of the negative asphericity of the surface of a first embodiment of the IOL according to the invention for the conversion of a spherical wave into another spherical wave and the negative asphericity of an outgoing wave measured in air and in the immersion medium in each case in dependence on the refractive power of the lens.

FIG. 4 shows the required negative asphericity of the surfaces ($asph_L$) of a first, biconvex, symmetrical embodiment of the IOL according to the invention for the conversion of an incoming wave with a spherical wave front (asphericity of the ingoing wave is $asph_{IN}=0$, that is to say for the extreme case of a topographical asphericity of the cornea, which is to be expected as a minimum, of −0.56) into an outgoing wave with an also spherical wave front (asphericity of the outgoing wave is $asph_{OUT}=0$). The asphericity of the surfaces of the IOL depends on the central surface refractive power of the IOL in the immersion medium. The data is shown in the lower curve (open circles).

In addition FIG. 4 (open triangles) shows the data of the negative asphericity of the wave front of the outgoing wave which is produced by a corresponding IOL in the immersion medium if the incoming wave has a plane wave front. The upper curve in FIG. 4 (open squares) shows the negative asphericity of the wave front of an outgoing wave which is produced by the same lens measured in air when a wave with a plane wave front is incident.

Figure 5:
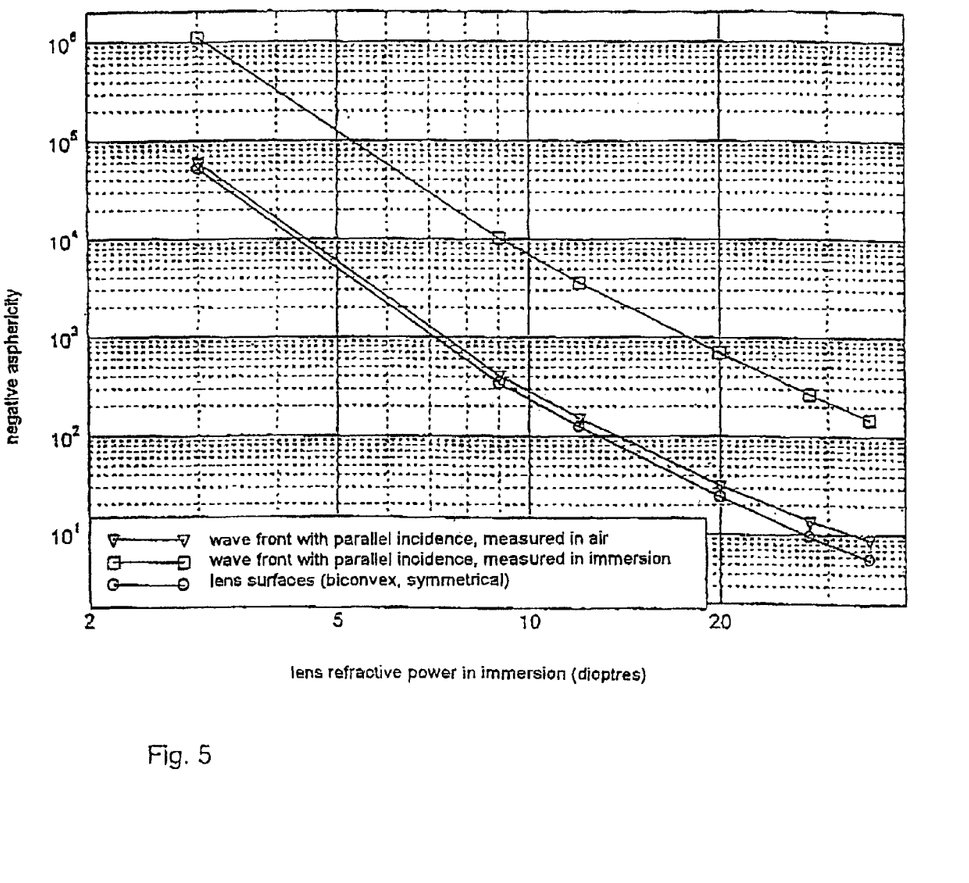
FIG. 5 shows a diagram of the negative asphericity of the surface of a second embodiment of the IOL according to the invention for the conversion of an aspherical wave into a spherical wave and the negative asphericity of an outgoing wave measured in air and in the immersion medium in each case in dependence on the refractive power of the lens.

FIG. 5 shows in a corresponding manner the negative asphericity of the surfaces of a biconvex, symmetrical IOL (open circles) $asph_L$, which is suitable for refracting an incoming aspherical wave with the maximum asphericity to be expected in the human eye, $asph_{IN}=11.4$, into a wave with a spherical wave front. The wave front of a plane incoming wave refracted by such a lens is shown in the two curves thereabove, namely for measurement in air (open triangles) and measurement in the immersion medium (open squares).

It is to be seen from FIGS. 4 and 5 that the topographical asphericities of the refractive surfaces of the intraocular lens according to the invention at any event assume negative values of less than −1 and the surfaces are therefore always hyperbolic. That applies in particular also in the case of an IOL according to the invention which has only one convex surface. If for example an IOL with a 20 dpt refractive power, a refractive index of 1.46 and a parameter p=12.3578 mm is selected, which is dimensioned for the case of a cornea with a 43 dioptres surface refractive power and an asphericity $asph_C=-0.26$, the asphericity of both surfaces of a biconvex mirror-symmetrical IOL $asph_L=-6.24$. In the case of an IOL whose entry surface is aspherical and whose exit surface is spherical, the asphericity of the one surface in contrast is $asph_L=-13.9$. The asphericity in the case of an IOL with only one hyperbolic-aspherical surface is in that case always greater than in the case of a symmetrical IOL. The asphericity values shown in FIGS. 4 and 5 represent minimum values in that sense. In all cases accordingly the asphericity of at least one of the refractive surfaces of the IOL according to the invention, with a refractive power in the immersion medium of $D_I>+3$ dpt, is less than −1. In other words the topography of at least one of the refractive surfaces can always be described by a hyperboloid.

It can also be seen from FIGS. 4 and 5 that such an IOL refracts an incoming plane wave into an outgoing wave with a hyperbolically curved wave front, because the wave front, for the asphericity of the outgoing wave $asph_{OUT}$ is in any event below −1. That applies both in the environment of the immersion medium with a refractive index $n_I=1.336$ (upper curves) and also in air with a refractive index (central curve). Preferably the hyperbolic wave front has an asphericity $asph_{OUT}<-5$.

A conventional IOL with spherically curved surfaces in contrast has a positive spherical aberration, that is to say it refracts an incoming wave with a plane wave front into an outgoing wave with an oblate elliptically curved wave front. That basically applies for a positive refractive power of the lens, that is to say both in air and also in the immersion medium, insofar as the refractive index of the lens material is greater than that of the environment medium, with a refractive index of the lens material of 1.46 in particular therefore also in the immersion medium.

Figure 6:
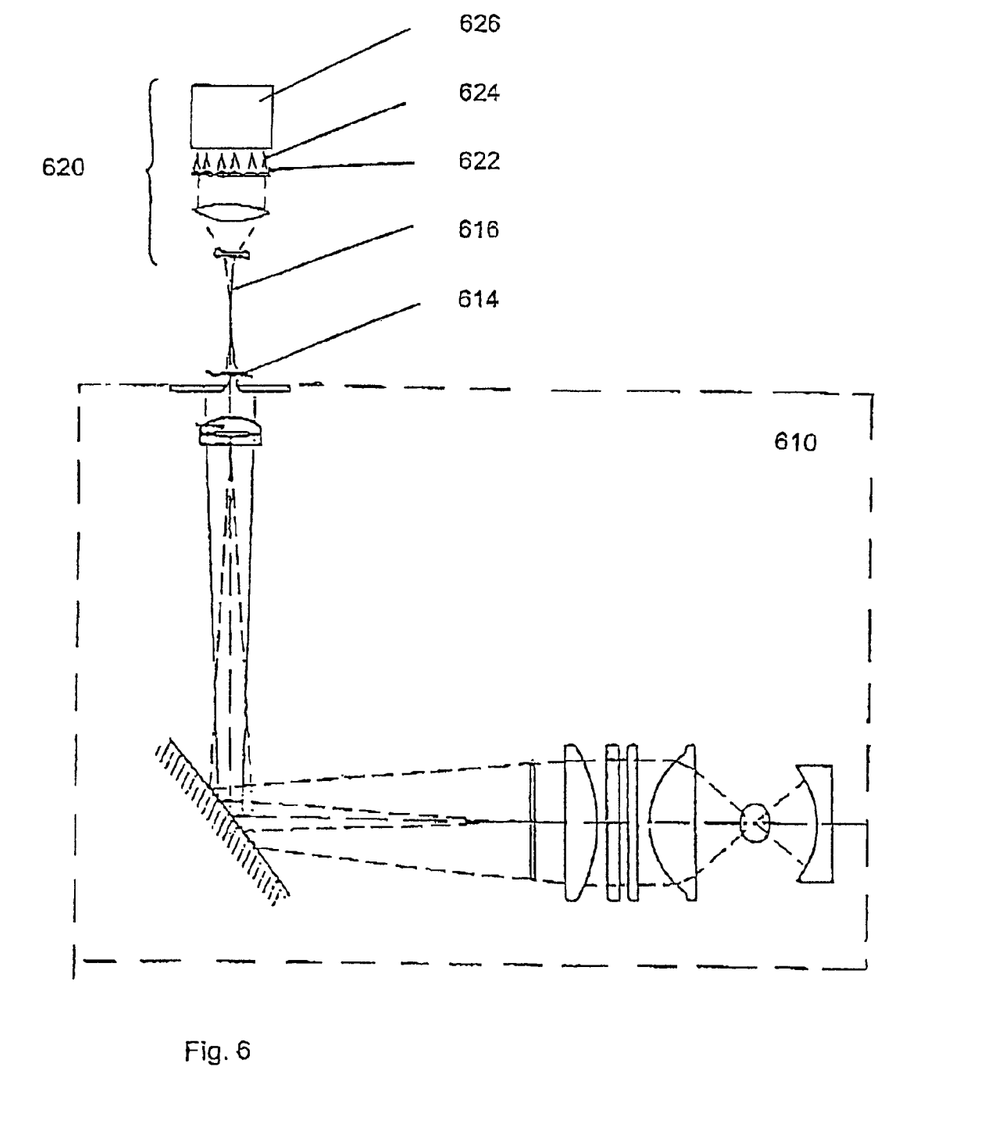
FIG. 6 is a diagrammatic view of a measuring apparatus for determining the waveform of the outgoing wave refracted by an IOL with incoming radiation of plane waves.

By virtue of a measurement of the waveform of the outgoing wave, an IOL according to the first embodiment of the present invention can be distinguished from an intraocular lens according to the state of the art when it is illuminated with a plane wave. And, more specifically, a suitable measurement can be effected in vitro in a standardised measuring structure and does not need to be implemented in the human eye. An example of such a measuring structure is shown in FIG. 6. It essentially corresponds to a setup 610 known from the ISO standard 11979-2, comprising an arrangement of optical elements for producing a plane wave, that is to say for producing and collimating a parallel beam with which an IOL 614 to be measured is illuminated. Disposed downstream thereof in the beam direction is a wave front analyser in accordance with Hartmann-Shack 620, for determining the waveform of the outgoing wave produced by the IOL 614. The wave front analyser breaks down the beam 616 coming from the IOL by means of a lens arrangement 622 into a plurality of beams 624 whose local distribution is detected by means of a light detector 626, such as for example a CCD camera. Conclusions about the waveform can be drawn in known manner on the basis of the distribution, by means of an image evaluation device (not shown). The imaging properties of the IOL to be investigated can be determined with that method. The results admittedly do not allow clear conclusions about the material properties and the topographical parameters of the intraocular lens as the same imaging properties can be achieved by intraocular lenses with different refractive indices and surface curvatures. However, in investigating the IOL, it is precisely the optical properties thereof that are important so that this method can be universally employed in contradiction with known methods in which evaluation is based on the topography of spherical lenses and which are therefore not suitable for measurement of the IOL according to the invention. Accordingly this measurement method is suitable in particular for distinguishing an IOL according to the invention from a conventional spherical IOL since, as indicated hereinbefore, it differs precisely by virtue of its characteristic imaging properties. Measurements of imaging properties of the IOL to be measured can preferably be implemented with this measurement setup in the ambient medium air, but also in the immersion medium.

In both of FIGS. 4 and 5 the refraction properties for intraocular lenses are selected with refractive powers in the range between 3 dpt and 35 dpt. The intraocular lenses according to the invention however are not limited to those refractive powers. Higher refractive powers can equally be selected and can be easily extrapolated on the basis of the steady configuration of the curves. The foregoing considerations were by way of example in respect of an IOL with a refractive index of 1.46, a diameter of 6 mm and an axis-parallel edge thickness of 0.25 mm. The invention however is not limited to an IOL with the stated values for the refractive index, diameter or edge thickness.

The IOL in accordance with a second embodiment of the present invention has a central refractive power in the immersion medium $D_I$ of a maximum of −2 dpt. Such an IOL according to the invention also refracts an incoming wave with an oblate elliptically curved wave front into an outgoing spherical wave, with suitable curvature for the lens surface, that is to say with a refractive power which decreases towards the lens edge (negative spherical aberration). Such a lens according to the invention converts an incoming plane wave into an outgoing wave with an oblate elliptically curved wave front.

As already mentioned a conventional spherical lens of positive refractive power converts an incoming plane wave into a wave with an oblate elliptically curved wave front, that is to say the refracted edge rays experience greater deflection than the central beams. In other words spherical lenses with a positive refractive power have a positive spherical aberration. Accordingly, aberration is negative in the case of a spherical lens with negative refractive power. Such a lens converts an incoming plane wave into an outgoing wave with an oblate elliptically curved wave front.

That can be seen from following Table 1 comparing the asphericities of outgoing waves after refraction of an incoming plane wave by intraocular lenses which are in accordance with the invention, and which are conventional, each with the same central (nominal) refractive power in immersion $D_I$ both for the environment medium air and also for the immersion medium.

TABLE 1

| $D_I$ of the IOL (in immersion) | | −2 dpt | −4 dpt | −7 dpt | −10 dpt |
|---|---|---|---|---|---|
| spherical IOL | asph$_{OUT}$ in immersion | +27.6 | +36.4 | +35.9 | +35.89 |
| | asph$_{OUT}$ in air | +3.55 | +3.63 | +3.63 | +3.65 |
| IOL according to the invention | asph$_{OUT}$ in immersion | +44143 | +7321 | +1521.3 | +559.4 |
| | asph$_{OUT}$ in air | +1807.9 | +302.49 | +64.03 | +23.9 |

In accordance with the data in Table 1, the wave fronts measured in the immersion medium have a positive asphericity which, depending on the refractive power of the lens, is 1600 to 20 times greater for the IOL according to the invention, than for a conventional spherical IOL. In the case of refraction in air the wave fronts produced by the IOL according to the invention, in comparison with the wave fronts produced by a conventional spherical lens, have a positive asphericity which is increased by 500 to 8.5 times, once again dependent in each case on the refractive power of the lenses. In particular the asphericity of a wave front produced by a spherical IOL with negative refractive power in air, independently of the magnitude thereof, does not reach any values which are greater than +10. The two outgoing waves can therefore be easily distinguished by measurement of their asphericity. With the refractive power of the lenses being known therefore once again it is possible by means of the apparatus shown in FIG. 6 to distinguish whether the lens being investigated is a conventional spherical IOL or an IOL according to the invention.

Figure 7:
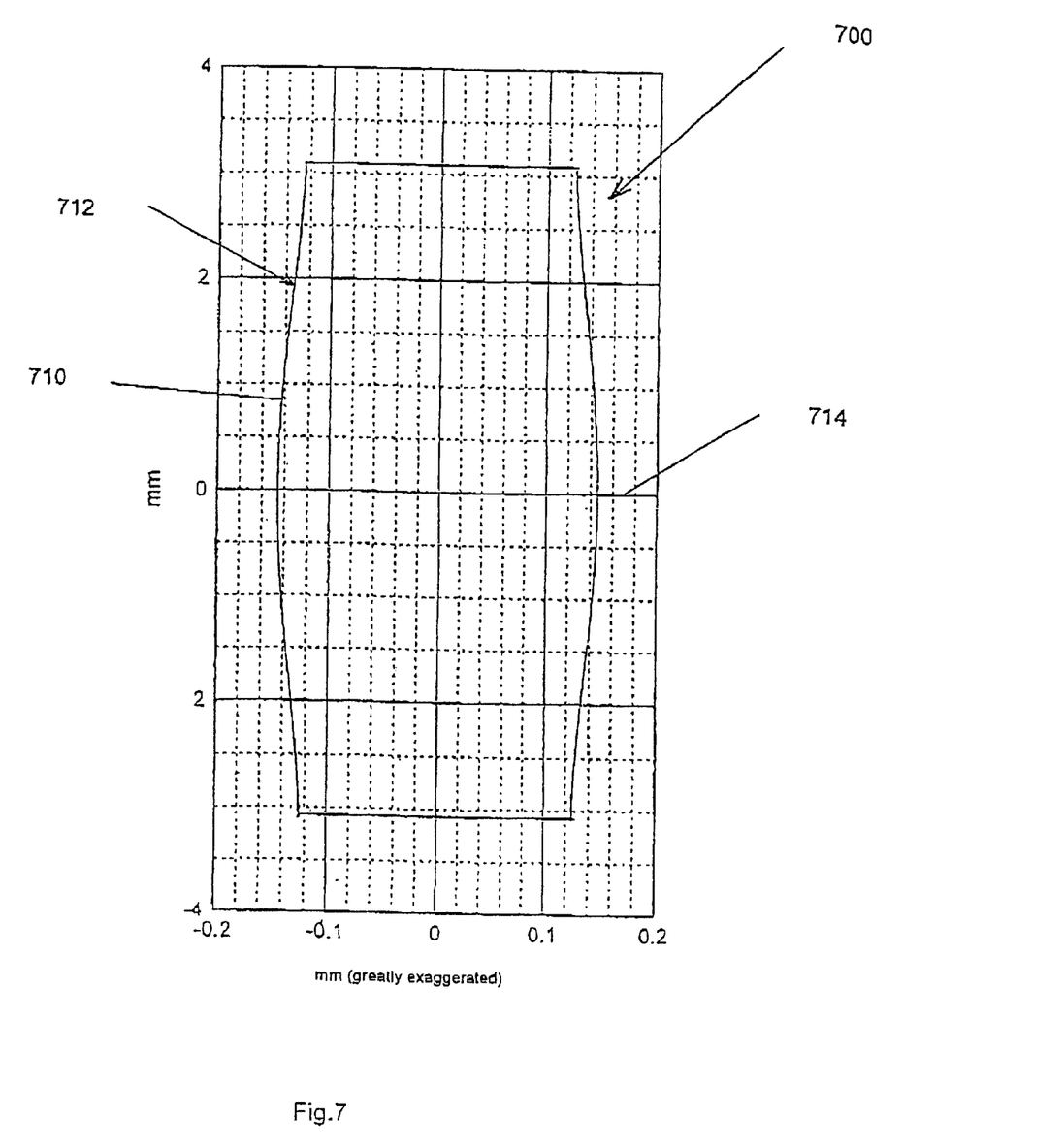
FIG. 7 shows a diagrammatic cross-section through a third embodiment of the IOL according to the invention.

An intraocular lens according to a third embodiment of the present invention has a central refractive power of between +2 dpt and −1 dpt in the immersion medium. In this case also the refractive power of the IOL according to the invention is lower at the edge than at the centre. FIG. 7 shows by way of example a symmetrical IOL 700 with a refractive power at the centre of +2 dpt, in cross-section. The lens 700 is designed to convert an incoming wave from the cornea with a wave front of elliptical asphericity asph$_{IN}$=5.51 into a substantially spherical wave. It will be seen that the meridian of the apex surface 710 of that IOL has an inflexion point 712 at a maximum spacing of about 1.8 mm from the central axis 714 of the lens.

Figure 8:
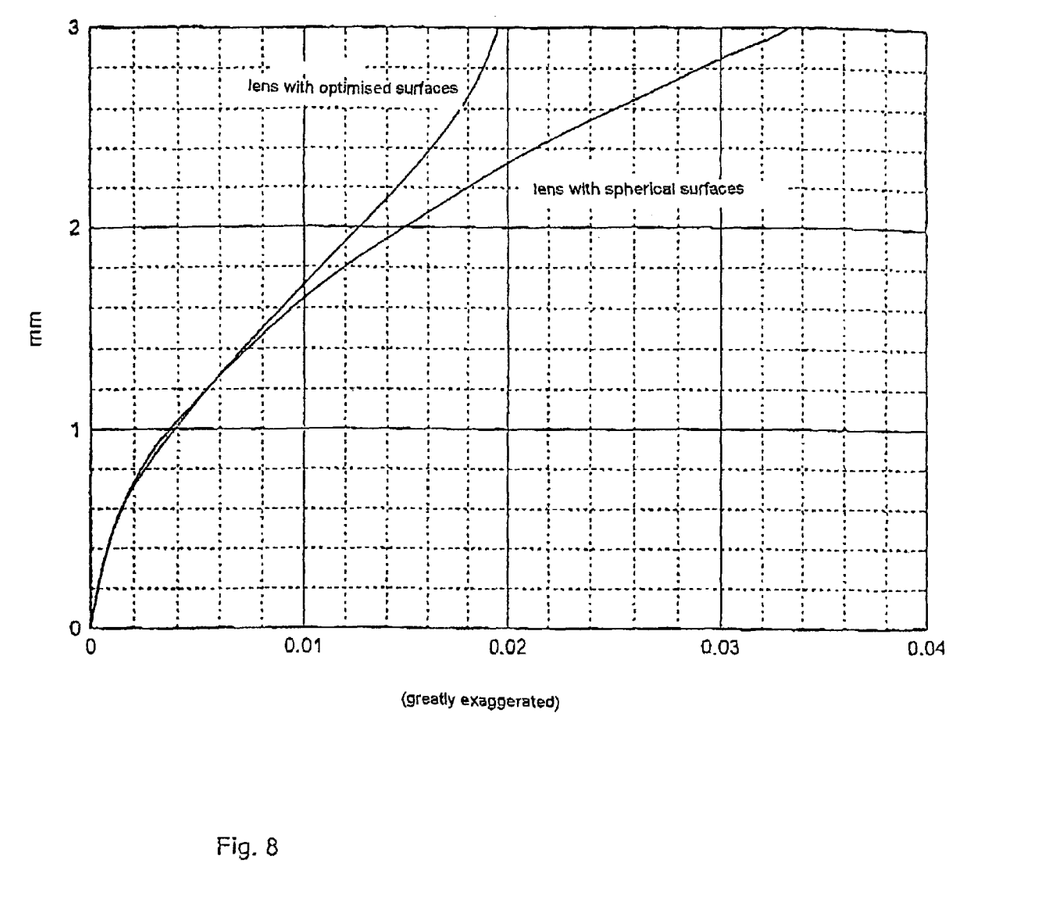
FIG. 8 shows the wave front of an outgoing wave from the IOL shown in FIG. 7 in comparison with an outgoing wave from a lens with spherical surfaces measured in air.
Figure 9:
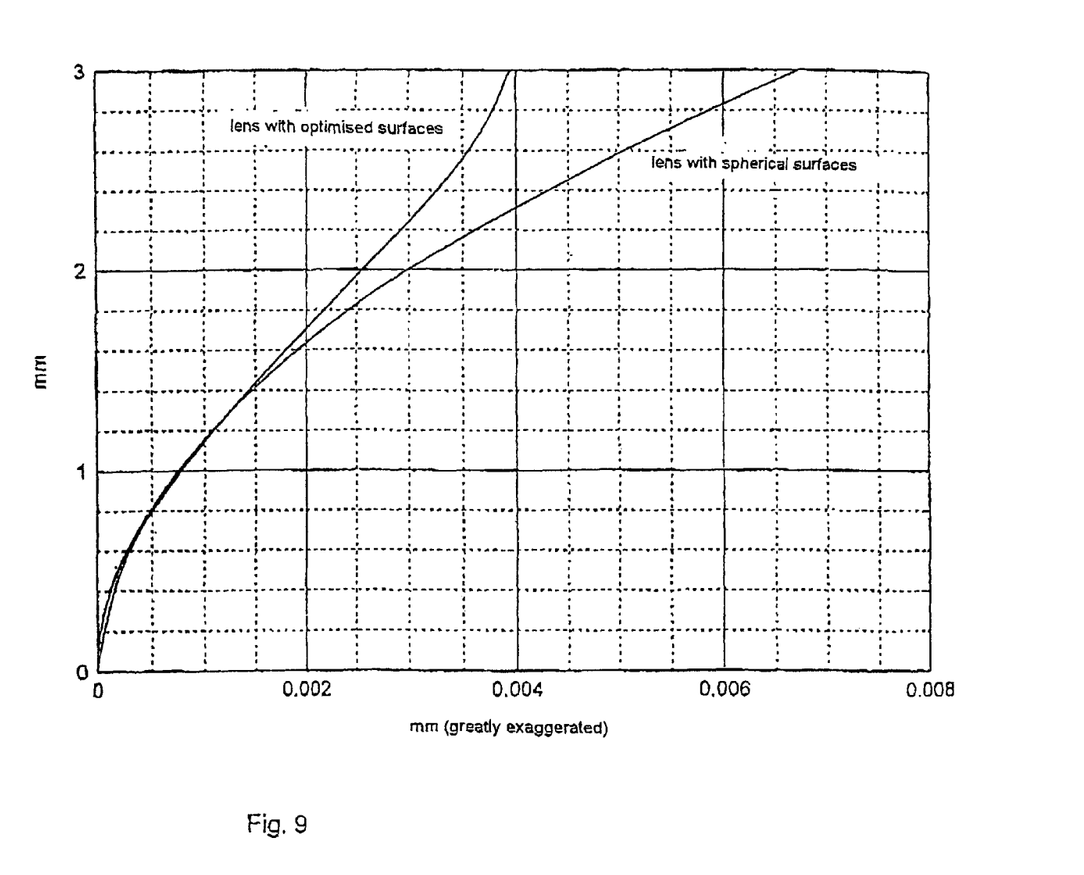
FIG. 9 shows the wave front of an outgoing wave from the IOL shown in FIG. 7 in comparison with an outgoing wave from a lens with spherical surfaces measured in the immersion medium.

FIGS. 8 and 9 show the wave fronts of outgoing waves, which are produced by the IOL according to the invention on the one hand and a spherical IOL with the same nominal refractive power on the other hand, when a plane wave is incident. It can be seen in the comparison that the meridian of the wave front produced by the IOL according to the invention has an inflexion point whereas the wave front produced by a conventional lens extends monotonically. That applies both in the environment medium air, see FIG. 8, and also in the immersion medium, see FIG. 9. In that way it is also possible to clearly distinguish lenses according to the invention with the above-mentioned refractive power from conventional, spherically curved lenses, by the method described with reference to FIG. 6.

What is claimed is:

1. An intraocular lens configured such that, in an in vivo environment of a human eye, an incoming wave with an elliptically oblately curved wave front is refracted into an outgoing wave with a spherical wave front, wherein refractive power in a center of the lens in the in vivo environment of the human eye is greater than or equal to +3 dpt, the intraocular lens comprises at least one convexly curved surface having a curvature which follows the function:

$$y^2 = 2px - (1+asph)x^2,$$

wherein x is a direction of light propagation or lens thickness, y specifies a direction perpendicular thereto, radially outwardly with respect to the center of the lens, p is a parameter and asph is asphericity, and wherein the curvature of the at least one convexly curved surface has an asphericity of less than −2.0, and wherein the intraocular lens is so designed that in an air environment, an incoming wave with a plane wave front is refracted into an outgoing wave with a hyperbolic wave front.

2. An intraocular lens according to claim 1, wherein the hyperbolic wave front has an asphericity of less than or equal to −5.

* * * * *